United States Patent [19]

Hashiguchi

[11] Patent Number: 4,576,147
[45] Date of Patent: Mar. 18, 1986

[54] HARD ENDOSCOPE WITH IMPROVED LIGHT DISPERSION

[75] Inventor: Toshihiko Hashiguchi, Sagamihara, Japan

[73] Assignee: Olympus Optical Co., Ltd., Tokyo, Japan

[21] Appl. No.: 634,673

[22] Filed: Jul. 30, 1984

Related U.S. Application Data

[63] Continuation of Ser. No. 395,662, Jul. 6, 1982, abandoned.

[30] Foreign Application Priority Data

Jul. 16, 1981 [JP] Japan .................................. 56-111448

[51] Int. Cl.$^4$ ................................................ A61B 1/06
[52] U.S. Cl. ........................................ 128/6; 350/96.26
[58] Field of Search .................................... 128/4–8; 350/96.26

[56] References Cited

U.S. PATENT DOCUMENTS

| | | | |
|---|---|---|---|
| 2,932,294 | 4/1960 | Fourestier et al. | 128/6 |
| 3,297,022 | 1/1967 | Wallace | 128/6 |
| 3,556,085 | 1/1971 | Takahashi | 128/6 |
| 4,072,147 | 2/1978 | Hett | 128/6 |
| 4,361,139 | 11/1982 | Takagi | 128/6 |

Primary Examiner—Edward M. Coven
Assistant Examiner—Max F. Hindenburg
Attorney, Agent, or Firm—Armstrong, Nikaido, Marmelstein & Kubovcik

[57] ABSTRACT

A hard endoscope is disclosed having a hard outer tube, an inner tube disposed eccentrically within the outer tube, such that a gap is left between the two tubes, the inner tube having an observing optical system disposed therein, a plurality of light guide fibers disposed within the gap, the light guide fibers being adapted to transmit light along the length thereof and an end surface formed by the termination of the outer tube, the inner tube, and the light guide fibers. The outer tube has a tip member disposed on the end thereof, the tip member having an opening and forming a curved inner peripheral surface. The inner tube has a tip member disposed on the end thereof, the tip member having a curved outer peripheral surface and a slit for receiving reflected light, and the inner tube tip member terminating at the abovementioned opening. The outer peripheral surface of the inner tube and the inner peripheral surface of the outer tube are curved in generally the same direction. The light guide fibers disposed between the two peripheral surfaces are also curved, curves thereof having various different curvatures, such that the light which is emitted therefrom is emitted in different directions.

7 Claims, 26 Drawing Figures

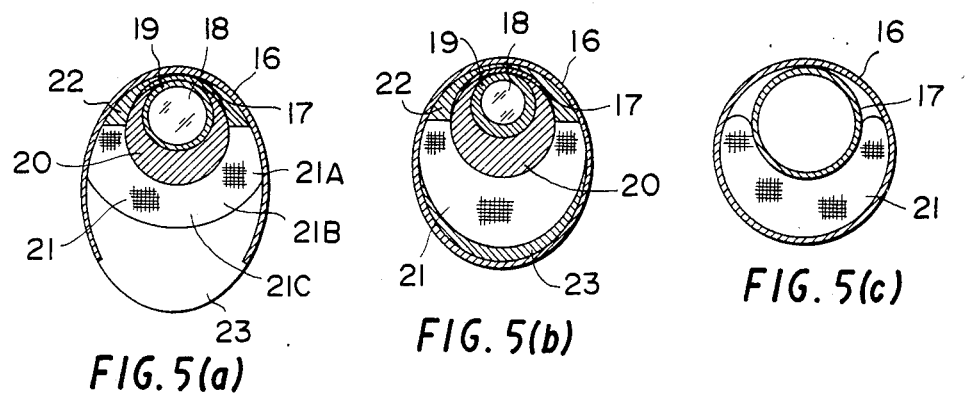
FIG. 5(a)　　FIG. 5(b)　　FIG. 5(c)
FIG. 6　　FIG. 7
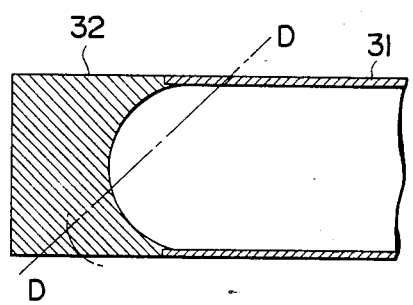 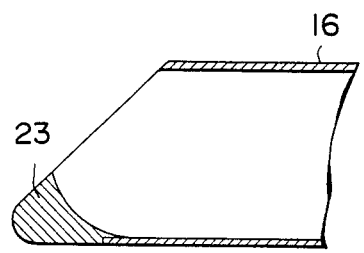
FIG. 8
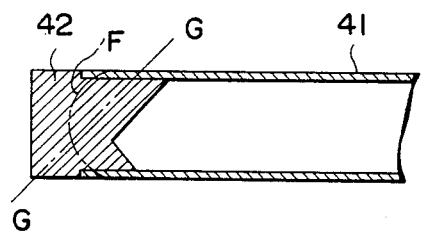

FIG.12
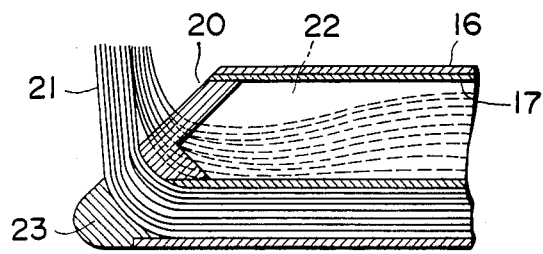
FIG.13
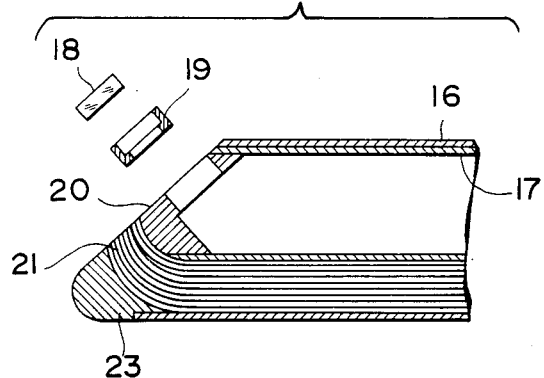
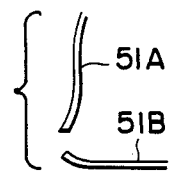
FIG.14(a)
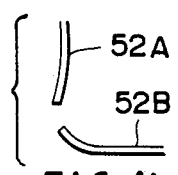
FIG.14(b)
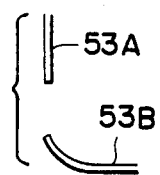
FIG.14(c)

HARD ENDOSCOPE WITH IMPROVED LIGHT DISPERSION

This application is a continuation, of application Ser. No. 395,662, filed July 6, 1982, abandoned.

BACKGROUND OF THE INVENTION

This invention relates to a hard endoscope which has projecting ends of light guides high in the light distribution characteristics of a formation wherein illuminating lights can be projected as widely dispersed out of the tip side of an inserted part to be inserted into a body cavity and in which the above mentioned formation can be comparatively simply manufactured.

Generally, in an endoscope with which an inserted part is inserted into a body cavity so as to be able to make an observation, diagnosis and treating therapy by using a forceps, an observing optical system and an illuminating optical system made to be able to observe an object are arranged on the tip side of the inserted part so that illuminating lights may be projected toward the object out of the projecting end of this illuminating optical system.

Light guides of bundled glass fibers are used for the above mentioned illuminating optical system. However, if the illuminating range projected out of the projecting ends of the light guides is narrow, the range which can be observed by using the observing optical system will be limited to be in a narrow range and therefore a part in which the objective position can not be well observed will be made and will be a great obstacle to the diagnosis.

BRIEF SUMMARY OF THE INVENTION

An object of the present invention is to provide a hard endoscope of a formation high in the light distribution characteristics wherein curvatures of respective fibers at projecting ends of light guides out of which illuminating lights are projected are arranged in a widely distributing form so as to be able to project the illuminating lights as widely dispersed.

Another object of the present invention is to provide a hard endoscope in which an illuminating optical system high in the light distribution characteristics is so formed as to be able to be realized by a simple structure and which can be manufactured at a low cost.

Further objects, features and advantages of the present invention will become apparent enough in the following explanation.

BRIEF DESCRIPTION OF THE DRAWINGS

FIG. 1 is a perspective view.

FIG. 2 is a sectioned view.

FIGS. 3 to 5 show a structure of a tip of an inserted part of an encoscope of a first embodiment of the present invention.

FIG. 3 is a general elevation of the first embodiment.

FIG. 4 is a magnified sectioned view showing the tip part in FIG. 3.

FIGS. 5(a), (b) and (c) are sectioned views in cut positions respectively on lines A—A, B—B and C—C.

FIGS. 6 to 10 show respective working steps and worked formations of the first embodiment.

FIG. 6 is a sectioned view showing a sectioned position of an outer tube material.

FIG. 7 is a sectioned view showing the cut, worked and formed outer tube in FIG. 6.

FIG. 8 is a sectioned view showing a cut position of an inner tube material.

FIGS. 11 to 13 show sectioned views showing assembling steps.

FIG. 11 is a sectioned view showing a step of inserting light guide fibers and the inner tube into the outer tube.

FIG. 12 is a sectioned view showing a step of forming light guide fiber end surfaces.

FIG. 13 is a sectioned view showing a step of attaching a cover glass.

FIGS. 14(a), (b) and (c) are respectively explanatory views showing in pairs shapes of light guide fibers in the respective arranged positions in the first embodiment as seen on the upper surface and elevation.

FIG. 15 is an explanatory view showing directions of illuminating lights as seen on the elevation.

FIG. 16 is an explanatory view showing directions of the illuminating lights as seen from above a perspective visual field.

DETAILED DESCRIPTION OF THE INVENTION

Figure 1:
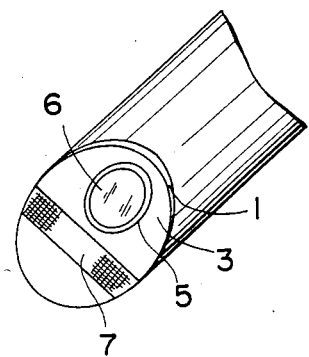
FIGS. 1 and 2 show a tip of an inserted part of a conventional endoscope.
Figure 2:
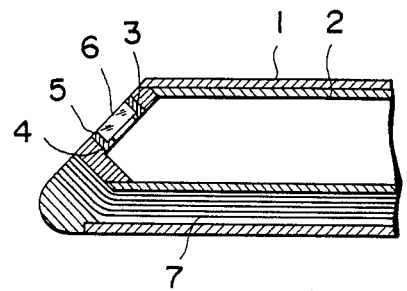

Prior to explaining the embodiments of the present invention, a conventional example of a hard endoscope shall be explained with reference to FIGS. 1 and 2.

Shown in these drawings is a perspective type hard endoscope wherein an inner tube 2 incorporating an observing optical system (not illustrated) is provided eccentrically within an outer tube in an inserted part and an inner tube tip member 3 forming an inclined surface in a direction at right angles with a perspective visual field direction of the observing optical system is arranged at the tip of this inner tube 2. An opening 4 is made in this inner tube tip member 3 and is fitted with a cover glass 6 through a frame 5. Further, the above mentioned inner tube tip member 3 is formed to be of an arcuate surface on the outer periphery on the sides of light guides 7 inserted and arranged on the outer periphery of the inner tube 2 so as to curve and arrange the projecting end sides of the light guides 7 in the perspective visual field direction.

Thus, in the structure of the tip of the inserted part of the conventional perspective type hard endoscope, the area through which the illuminating lights are projected out of the projecting ends of the light guides 7 is small, the illuminating lights are not projected as well diffused out of the projecting end surfaces, the illuminated range is narrow and the light distribution characteristics are low.

The present invention is made to solve the problems of the above mentioned conventional example.

Embodiments of the present invention shall be explained in the following with reference to FIG. 3 and other drawings following it.

Figure 3:
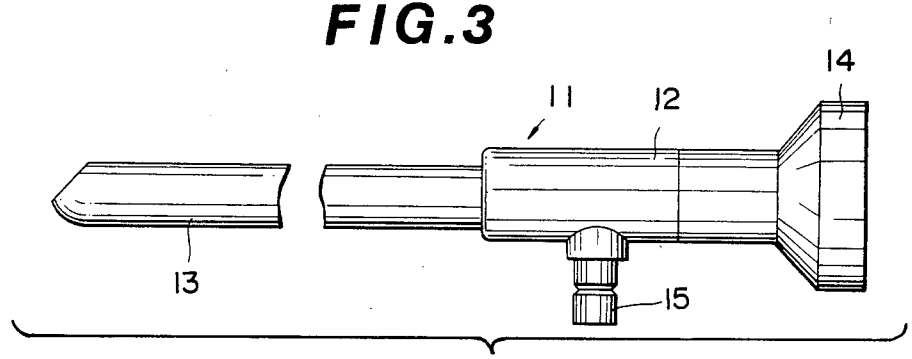
Figure 4:
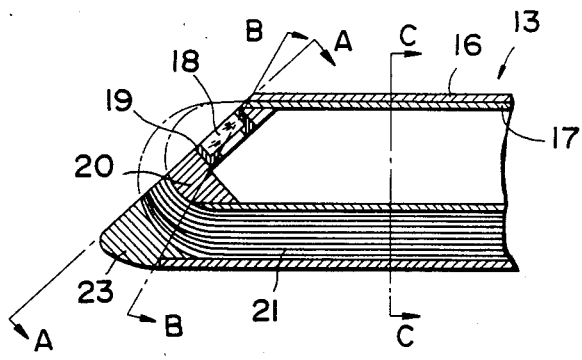

FIGS. 3 to 5 show a first embodiment of the present invention. This embodiment relates to a perspective type hard endoscope. In these drawings, the reference numeral 11 denotes a hard endoscope comprising an operating part 12 and an inserted part 13. The operating part 12 has an eyepiece part 14 and a light guide cable connecting joint 15. The inserted part 13 has an inner tube 17 provided eccentrically within an outer tube 16. An observing optical system (not illustrated) is contained in this inner tube 17.

An inner tube tip member 20 supporting and fixing a frame 19 fitting and fixing a cover glass is secured with a bonding agent or by soldering to an opening at the tip of the above mentioned inner tube 17. This inner tube tip member 20 is hemispherical with the outside diameter of the inner tube 17 as a diameter and is partly cut to form a perspective visual field surface. Many light guide fibers 21 transmmitting and projecting illuminating lights are arranged and contained in an air space substantially meniscus-shaped in the section and formed between this inner tube 17 and the outer tube 16 eccentrically containing the inner tube 17. These light guide fibers 21 are once squeezed and converged by a pressing member 22 fixed on the outer periphery near the tip of the inner tube 17 and are strongly fixed as curved so as to have various curvatures in the respective parts of the projecting end surfaces.

The above mentioned light guide fibers 21 are cut and ground so that the projecting end surfaces may be flush with the perspective visual field surface, their inner peripheral surfaces are curved near the projecting end surfaces along the outer periphery of the inner tube tip member 20 and their outer peripheral surfaces are contained so as to contact the inner surface of the outer tube 16 to which a tip member 23 having a surface flush with the above mentioned perspective visual field surface is attached.

The hemispherical center of the above mentioned inner tube tip member 20 is eccentric from the hemispherical center of the tip of the outer tube 16 and the light guide fibers 21 are contained as curved so as to have various curvatures in the respective parts of the projecting end surfaces. These light guide fibers 21 as contained are shown in FIG. 5. FIGS. 5(a), (b) and (c) are explanatory sectioned views respectively showing the section shown by the reference symbol A—A (which shows the perspective visual field surface substantially at the tip of the inserted part 13), the section in the position shown by the reference symbol B—B and the section in the position shown by the reference symbol C—C.

The steps of working and assembling the endoscope tip having such structure as in the above shall be explained with reference to the drawings.

FIGS. 6 and 7 show respectively a formation and completed product in the step of manufacturing the outer tube 16 of the inserted part 13 of the above described structure.

First, as shown in FIG. 6, a columnar tip member material 32 in which a hemispherical recess is formed is fixed by soldering or with a bonding agent to an opening tip of a cylindrical outer tube material 31, is then cut in the position shown by the reference symbol D—D so as to have a predetermined perspective visual field surface and is further formed to be round as shown by the illustrated one-point chain line at the corner to form such tip member 23 and outer tube 16 as are shown in FIG. 7.

Figure 9A:
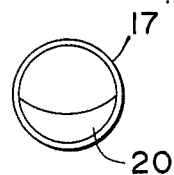
FIGS. 9(a), (b) and (c) are respectively a side view, sectioned view and perspective view of the cut, worked and formed inner tube in FIG. 8

On the other hand, the formation of the inner tube 17 and inner tube tip member 20 shall be explained with reference to FIGS. 8 to 10.

The cylindrical inner tube material 41 is cut in the opening tip part so that a columnar inner tube tip member 42 having a diameter equal to the outside diameter of this inner tube material 41 may fit in a part of the outer periphery with the inner tube material 41. At the same time, a cut surface parallel with the predetermined perspective visual field surface on which the cover glass 18 (See FIG. 4) is to be fitted and fixed and a cut surface substantially at right angles with this cut surface are formed on the tip part to be inserted into the inner tube material 41.

Figure 9B:
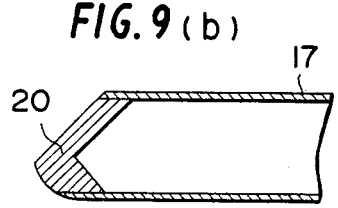
Figure 9C:
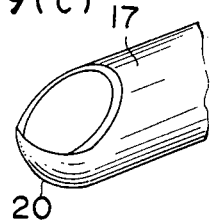

This inner tube tip member 42 and the inner tube material 41 are fitted and fixed together, are then hemispherically cut and shaped as shown by the one-point chain line F and are then cut off in the position and direction to be the visual field surface as shown by the reference symbol G—G to form such inner tube 17 as is shown in FIG. 9.

FIGS. 9(a), (b) and (c) show respectively a side view, sectioned elevation and perspective view of the inner tube 17 to which the inner tip member 20 (shown by the reference numeral 20 more particularly with a hole further formed) of the tip formed in the above mentioned steps is attached and fixed.

Figure 10A:
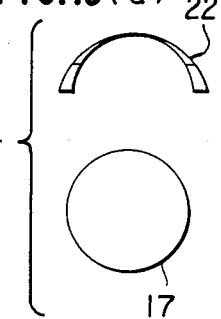
FIGS. 10(a), (b) and (c) are respectively a disassembled side view, disassembled elevation and perspective view for explaining a step of providing a pressing member in the inner tube.
Figure 10B:
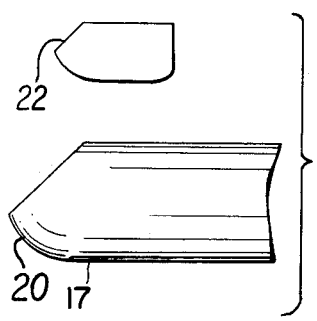

A pressing member 22 of such shape as of a saddle as shown in FIG. 10 is fixed by soldering or the like to the upper part of the tip of the above mentioned inner tube 17 (the upper part illustrated here is the part most adjacent to the outer tube 16 when the inner tube is contained eccentrically in the outer tube 16).

Figure 10C:
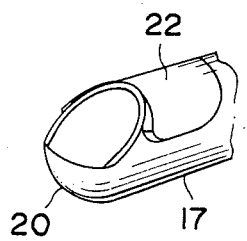

The inside and outside surfaces of the above mentioned pressing member are formed so as to respectively have the same curvatures as of the outer periphery of the inner tube 17 and the inner wall of the outer tube 16. As the centers of these curvatures are eccentric from each other, the pressing member is thinnest in the middle part and is thickest on both peripheral side parts. This pressing member 22 is fixed so as to be flush at the front end with the visual field surface as shown in FIG. 10(c). Both peripheral side parts thickened as mentioned above are so cut near the visual field surface as to have a proper curvature to improve the light distribution characteristics of the light guide fibers 21 on the projecting end surfaces (See FIGS. 10(b) and (c)).

Figure 11:
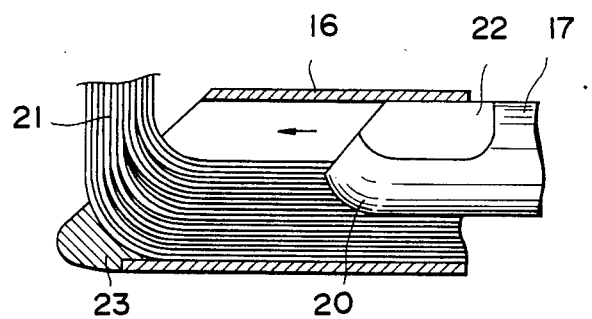

Then the light guide fibers 21 are inserted as shown in FIG. 11 into the outer tube 16 formed as described above and then the above mentioned inner tube 17 is inserted into the outer tube 16 as indicated by the arrow and is fixed in a position in which both visual field surfaces of the outer tube 16 and inner tube 17 are flush with each other as shown in FIG. 12. Then the light guide fibers 21 are fixed at the tips, are cut along the visual field surface and are ground on the end surfaces. The above mentioned light guide fibers 21 are once squeezed near the tips by the pressing member 22 as illustrated and are arranged so as to have various curvatures in the respective parts.

Then a hole is made in the inner tube tip member 20 having a predetermined thickness and the cover glass 18 fitted and fixed in the frame 19 is inserted into the above mentioned hole and is fixed with a bonding agent or the like (See FIG. 13).

In the above mentioned first embodiment completed by such steps as in the above, the light guide fibers 21 contained in the air space substantially meniscus-shaped in the section between the outer tube 16 and the inner tube 17 eccentrically provided in the outer tube 16 are different in the shapes (such as the curvatures) near the projecting end surfaces in the respective contained parts as shown in FIG. 14.

FIGS. 14(a), (b) and (c) show respectively the shapes near the projecting ends as seen on the upper surfaces and elevations of the light guide fibers 21 having the projecting ends in the positions shown by the respective reference numerals 21A, 21B and 21C in FIG. 5(a). The shapes are as shown by 51A and 51B; 52A and 52B; 53A and 53B.

Figure 15:
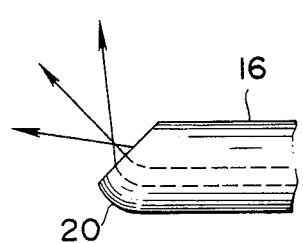
FIGS. 15 and 16 show light distribution characteristics in the first embodiment.
Figure 16:
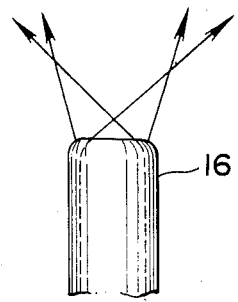

Therefore, in this case, the light distribution characteristics of the illuminating lights projected out of the projecting ends of the light guide fibers 21 will be as shown in FIGS. 15 and 16.

FIGS. 15 and 16 show respectively the ligiht distribution characteristics by the light guide fibers 21 as seen respectively on the elevation and upper surface of the inserted part 13 in the above mentioned first embodiment. The light guide fibers 21 are so arranged and contained as to be able to project lights uniformly in a wide range in various directions from respective parts out of the projecting surfaces as indicated by the arrows.

Therefore, if the hard endoscope high in the light distribution characteristics of the structure in this embodiment is used, a wide range will be able to be illuminated and the organs and the like within the body cavity will be able to be well observed.

Further, according to the above mentioned working steps, the number of steps can be reduced to be less than in the conventional example and the number of component parts can be also reduced to the advantage of the manufacture and maintenance.

Figure 17:
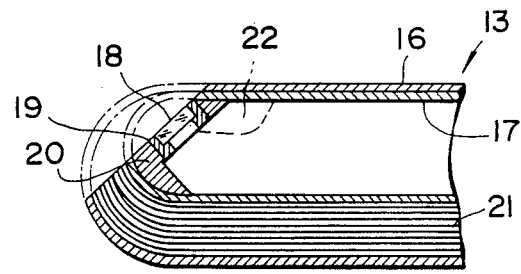
FIG. 17 is a senctioned view showing a structure of a second embodiment of the present invention.

FIG. 17 shows a structure of a hard endoscope tip of a second embodiment of the present invention.

In this embodiment, an outer tube member and inner tube member hemispherial at the tips as shown by the one-point chain lines to make the above described tip member 23 unnecessary are used and the outer tube 16 and inner tube 17 are formed by being partly cut at these tips and the inner tube tip member 20 of substantially the same shape as of the above described first embodiment is inserted and fixed in the above mentioned cut inner tube 17 tip. This inner tube tip member 20 is so formed as to have a cut surface parallel with the visual field surface and having a predetermined thickness and a cut surface substantially vertical to this surface as illustrated by cutting a bar fitting the inner surface of the inner tube 17 and hemispherical at the tip. An inserting hole is made on the cut surface parallel with the above mentioned visual field surface. The frame 19 in which the cover glass 18 is fitted and fixed is inserted and fixed in this hole. Glass 18 and frame 19 form part of the tip surface including the projecting end surfaces of light guide fibers 21 of this embodiment. The pressing member 22 improving the light distribution characteristics is fixed to the outer periphery of the inner tube 17 tip the same as is described above.

According to this embodiment, the above described tip member 23 is made unnecessary and it is made easy to form and fix the inner tube tip member 20.

In some case, even if the above mentioned inner tube tip member 20 is made to be only of a parallel cut surface forming a part of the perspective visual field surface, it will be able to well have a required strength.

According to this embodiment, not only there are such excellent light distribution characteristics as in the above described first embodiment but also the numbers of the component parts and manufacturing steps can be reduced and therefore the product cost can be made low.

Figure 18:
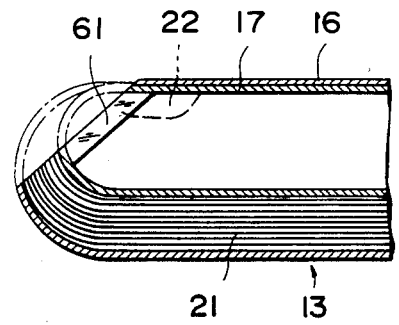
FIG. 18 is a sectioned view showing a structure of a third embodiment of the present invention.

By the way, in the above mentioned second embodiment, a cover glass 61 having a predetermined thickness and fitted in the spherical inner tube cut at the tip may be provided on the perspective visual field surface as in a third embodiment shown in FIG. 18 without providing the inner tube tip member 20.

Thus, the numbers of the component parts and manufacturing steps can be further reduced and therefore the product cost can be made lower.

In the above described embodiment, it is mentioned that the hard endoscope tip is formed by partly cutting the inner tube 17 and outer tube 18 hemispherical at the tips. However, even if the perspective visual field surface is formed by cutting the inner tube 17 and outer tube 18 having conical or parabolic curved surfaces to form the hard endoscope tip, a hard endoscope high in the light distribution characteristics will be able to be realized.

It is apparent that working modes different in a wide range can be formed without deviating from the spirit and scope of the present invention. The above mentioned working modes other than are limited inthe claims of the present invention are included in the scope of the present invention.

I claim:

1. A hard endoscope, comprising:
a hard outer tube having an inner peripheral surface;
an inner tube disposed eccentrically within said outer tube such that said inner tube contacts a portion, defined as the upper portion, of said inner peripheral surface of said outer tube, thereby forming a cresent-shaped space in cross-section, between the inner peripheral surface of said outer tube and the outer surface of said inner tube,
an observing optical system disposed within said inner tube;
a plurality of light guide fibers disposed within said space for transmitting light therealong;
a tip surface for emitting and receiving light, said tip surface disposed on a tip part formed by the inner and outer tubes, said tip part having an eliptical upper surface and a visual field direction forward of said tip surface;
an end portion of said inner tube disposed at the tip part, said end portion having a curved outer surface in contact with said light guide fibers;
an end portion of said outer tube disposed at the tip part, said end portion having at its lower side, diametrically opposite the upper portion of the tube, an inner curved surface in contact with said light guide fibers; and
a saddle-shaped pressing part disposed in between said inner and outer tubes at the upper portions thereof and near said tip part, said pressing part having edges for pressing said light guide fibers together in the circumferential direction with respect to said inner tube, such that said light guide fibers are concentrated in the visual field direction.

2. The hard endoscope of claim 1, wherein said end portion of said inner tube is integral with said inner tube.

3. The hard endoscope of claim 1, wherein said end portion of said outer tube is integral with said outer tube.

4. The hard endoscope of claim 1, wherein the curved surfaces of said end portions are partial parabaloids.

5. The hard endoscope of claim 1, wherein the curved surfaces of said end portions are partial spheres.

6. The hard endoscope of claim 1, wherein the outer surface of the tip part is formed by the outer peripheral surface of said end portion of said outer tube.

7. A hard endoscope, comprising:
   a hard outer tube having an inner peripheral surface;
   an inner tube disposed eccentrically within said outer tube such that said inner tube contacts a portion, defined as the upper portion, of said inner peripheral surface of said outer tube, thereby forming a cresent-shaped space in cross-section, between the inner peripheral surface of said outer tube and the outer surface of said inner tube,
   an observing optical system disposed within said inner tube;
   a plurality of light guide fibers disposed within said space for transmitting light therealong;
   a tip surface for emitting and receiving light, said tip surface disposed on a tip part formed by the inner and outer tubes, said tip part having an eliptical upper surface and a visual field direction forward of said tip surface, said tip surface presenting said light guide fibers in a crescent-like shape so as to increase illumination around the observing optical system;
   an end portion of said inner tube disposed at the tip part, said end portion having a curved outer surface in contact with said light guide fibers;
   an end portion of said outer tube disposed at the tip part, said end portion having at its lower side, diametrically opposite the upper portion of the tube, an inner curved surface in contact with said light guide fibers; and
   a saddle-shaped pressing part disposed in between said inner and outer tubes at the upper portions thereof and near said tip part, said pressing part having edges for pressing said light guide fibers together in the circumferential direction with respect to said inner tube, such that said light guide fibers are concentrated in the visual field direction.

* * * * *